United States Patent [19]

Beard et al.

[11] Patent Number: 5,196,799
[45] Date of Patent: Mar. 23, 1993

[54] METHOD AND APPARATUS FOR TESTING A PROTECTIVE BARRIER MATERIAL FOR PINHOLES AND TEAR STRENGTH

[75] Inventors: Richard B. Beard, Atco, N.J.; Robert Schmukler, Rockville, Md.; Herman P. Schwan, Radnor; Frederick Prout, Huntingdon Valley, both of Pa.

[73] Assignees: Drexel University, Philadelphia, Pa.; United States of America as represented by the Food & Drug Administration, Rockville, Md.

[21] Appl. No.: 552,284

[22] Filed: Jul. 12, 1990

[51] Int. Cl.$^5$ .................. G01R 27/00; G01R 27/26
[52] U.S. Cl. ................... 324/557; 324/675; 324/693
[58] Field of Search ............ 324/557, 558, 551, 133, 324/554, 693, 699, 663, 671, 674, 675, 655; 340/605; 73/40, 45.5

[56] References Cited

U.S. PATENT DOCUMENTS

| | | |
|---|---|---|
| 2,221,323 | 11/1940 | Gammeter . |
| 2,244,591 | 6/1941 | Youngs et al. .................. 324/558 X |
| 2,297,837 | 10/1942 | Loughnane .......................... 324/557 |
| 2,503,992 | 4/1950 | Becker ............................. 324/558 X |
| 2,622,129 | 12/1952 | Killian . |
| 3,155,898 | 11/1964 | Chope ............................. 324/674 X |
| 3,462,682 | 8/1969 | Barnett et al. . |
| 3,519,922 | 7/1970 | Nash et al. ...................... 324/675 X |
| 3,543,924 | 12/1970 | Ryan et al. . |
| 3,992,766 | 11/1976 | Field . |
| 4,099,117 | 7/1978 | Erath .................................. 324/557 |
| 4,229,645 | 10/1980 | Vigano et al. . |
| 4,345,204 | 8/1982 | Shelley ............................... 324/663 |
| 4,387,336 | 6/1983 | Joy et al. . |
| 4,563,633 | 1/1986 | Johnson et al. . |
| 4,810,971 | 3/1989 | Marable ............................. 324/557 |

Primary Examiner—Jack B. Harvey
Attorney, Agent, or Firm—Panitch Schwarze Jacobs & Nadel

[57] ABSTRACT

A method and apparatus for the non-destructive testing of a protective barrier material. In a preferred embodiment, the method comprises applying an alternating electrical current across the protective barrier material for establishing a conductivity, G, of the protective barrier material and/or a quality factor, Q, of the protective barrier material. The conductivity, G, and/or the quality factor, Q, are measured at more than one frequency. The quality factor and/or conductivity measurements so obtained at the more than one frequency are compared to predetermined quality factor and/or conductivity limits.

34 Claims, 1 Drawing Sheet

FIG. 1
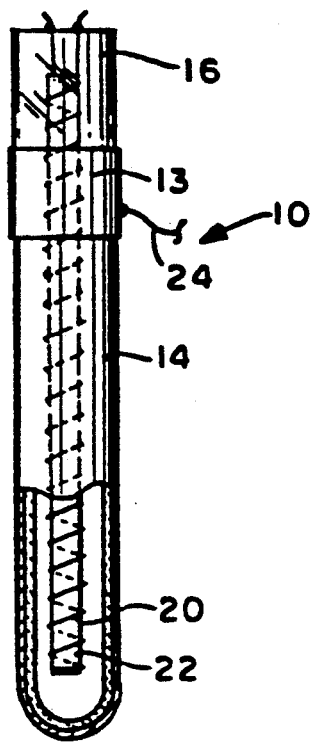
FIG. 2
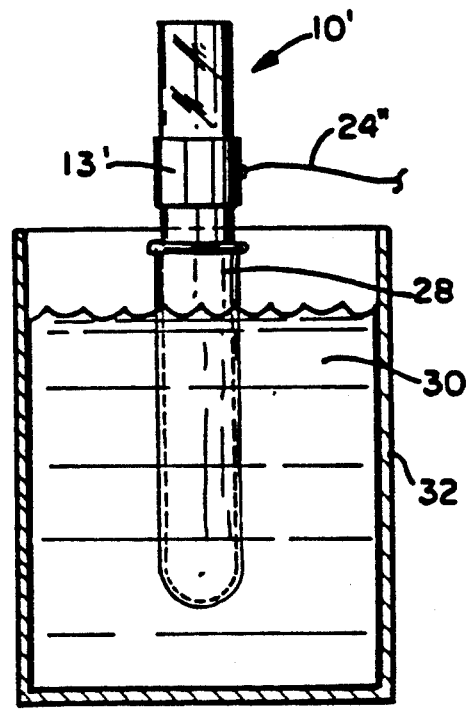
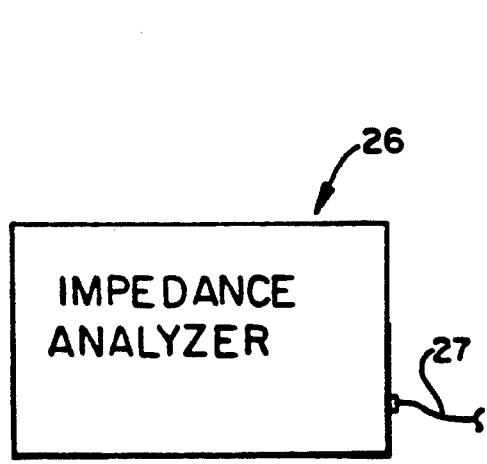
FIG. 3
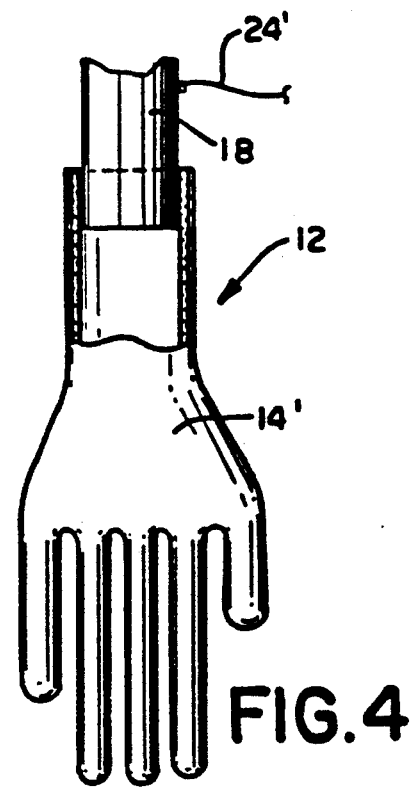
FIG. 4

METHOD AND APPARATUS FOR TESTING A PROTECTIVE BARRIER MATERIAL FOR PINHOLES AND TEAR STRENGTH

STATEMENT OF GOVERNMENT INTEREST

The invention described herein was made in part in the course of work under a Cooperative Research and Development Agreement (CRADA) with the Food and Drug Administration (FDA).

FIELD OF THE INVENTION

The present invention relates to a method and apparatus for the non-destructive testing of a protective barrier material, for example, a condom, a glove, or encapsulation or packaging, for the detection of small-sized holes, in the micron and sub-micron diameter range. More particularly, the present invention relates to the non-destructive testing of such a protective barrier material comprising applying an alternating electrical current across the protective barrier material, measuring the conductivity and/or quality factor of the protective barrier material and comparing the measured conductivity and/or quality factor to predetermined limits.

BACKGROUND OF THE INVENTION

There is great concern among world health organizations and certain regulatory agencies regarding the quality levels of protective barrier materials or products, for example, condoms and gloves. This concern is due to the urgent need to protect users of the barrier materials against the transmission of fluid transmitted diseases, for example, the AIDS virus, having a diameter of about 0.1 micron ($\mu$), and the herpes virus, having a diameter of about 0.12 to about 0.15$\mu$. The greatest concerns are for freedom from bursting and/or tearing of the barrier materials during use and freedom from the presence of holes, for example, pinholes which are large enough to permit transmission of viruses, which may allow the transmission of such diseases. Accordingly, the present invention has been developed for the testing of the integrity of such protective barrier materials. In particular, the present invention has been developed for the non-destructive testing of protective barrier materials for holes having a diameter less than a micron.

Manufacturing high quality condoms, gloves and other barrier material products requires a well-trained technical staff and special production equipment. Most large condom manufacturing plants are highly automated and have been custom designed by the individual condom manufacturer.

Vulcanization processes for rubber were developed in the late nineteenth century. This enabled the substitution of rubber for animal membranes in the manufacture of condoms. Dissolved rubber was initially used as the raw material for condoms. However, since the stabilization of dissolved rubber particles was poor, a high percentage of defective condoms were initially produced. In the 1930's, production of condoms from liquid natural rubber latex revolutionized the rubber and condom manufacturing industries.

During the current manufacture of condoms, concentrated and stabilized latex is placed in dipping tanks into which glass or metal condom-shaped molds, or mandrels, are dipped by means of a continuous conveyor system. The molds are then carried through a tank containing cooled latex and are placed into drying ovens. The latex-covered molds are then dipped into a second tank of latex. A brush rolls a ring on the open end of the condom and the molds are then conveyed into ovens for further drying and vulcanization. The condoms are then stripped from the molds by water jets or brushes and the condoms are tested for integrity.

While rubber condoms or gloves are generally produced in various sizes using molds, testing is carried out on mandrels also of different sizes. Rubber membranes can be produced as thin as 0.02 millimeter (mm). However, most rubber membranes are produced having a thickness of about 0.04 to about 0.07 mm. The thinner the membrane, the greater the sensitivity for the user. However, thicker membranes are stronger and less likely to have holes, thereby having higher and therefore more acceptable quality levels.

Currently, there are two primary types of testing procedures utilized for testing condoms: hydraulic and electrical procedures. The hydraulic and electrical tests are both influenced by the surface properties of the latex (the most common condom material) and the surface energy of the liquid which is used in the tests. The wettability of any pore surface of a condom is the primary determinant of the formation of a fluid pathway across a condom. Thus, the testing of condoms for integrity from defects, for example, holes, depends on the state of the interface.

According to the American Society for Testing and Materials (ASTM D3492-83) hydraulic test, the condom is filled with about 300 milliliters (mL) of water and is then visually inspected for water leakage. The FDA uses a modified version of the ASTM hydraulic test in which the condom is filled with 300 mL of water and the open end is then closed. The water-filled condom is then rolled on a water-absorbent material, which is subsequently visually inspected for spots of water.

Condoms are also tested individually using an electrical screening process. Unfilled latex rubber, such as the latex rubber used in condoms, is a very poor electrical conductor so that electrical current generally does not pass through an unflawed or defect-free condom. In the electrical screening process, condoms are rolled by hand onto tube-shaped electrodes or mandrels and are then passed through an electrolyte solution (wet system) or across a fine mesh screen (dry system) during the application of an electrical potential between the electrode and the electrolyte or screen. A condom is rejected if current passes through it and/or the current increases.

As indicated, the electrical screening tests fall into two categories: dry and wet electrical tests. The dry electrical test comprises a high voltage dielectric breakdown test, wherein a condom is mounted on a metal mandrel (the inside electrode) and is subjected to a high voltage from an outside electrode. The dry electrical test is actually a semi-destructive test, since failed condoms are generally irreversibly damaged.

There are several different varieties of tests which may be considered wet electrical tests. However, all of the wet electrical tests directly or indirectly measure the resistance across a hole in the condom. The resistance is measured directly by measuring the direct current (d.c.) resistance of a condom-covered mandrel to the metal tank containing an electrolyte, and indirectly, by measuring the voltage remaining on a charged condom-covered mandrel after an elapsed time period.

D.C. resistance measurement is the industry standard used today for hole and potential leakage testing. However, this method is subject to secondary effects, namely, large d.c. polarization and interfacial resistance effects at the membrane holes. Moreover, the magnitude of the secondary effects increases as the hole becomes smaller, resulting in a greater uncertainty in the measurement. Thus, smaller holes, for example, pinholes with a diameter in the micron or sub-micron range, have a considerable increase in their effective d.c. resistance. This makes it more difficult to detect such pinholes using such a d.c. resistance measurement method. In particular, the reliability of d.c. resistance measurement for defect detection at the level required for protection against the AIDS virus and other sub-micron-sized viruses is now being questioned by the regulatory agencies and other health organizations.

In addition, resistance tests have sometimes been used as laboratory tests for lot assessment. Laboratory measurements on commercially available condoms have demonstrated that in a given production lot, there may be some condoms with small and large holes, while in another given lot, there may not be any defective condoms. Thus, reliable testing of each condom is needed.

With the current electrical testing methods, the magnitude of the impedance of the barrier material is measured. However, these tests include the reactive component of that impedance which is due to the capacitance of the condom. Furthermore, in most instances, manufacturers use simple tap water as the electrolyte in their electrical tests. Tap water is quite resistive and the detection limit for holes in the barrier material increases to about 60$\mu$ to about 80$\mu$. The present invention is directed to overcoming the shortcomings of prior art testing techniques for protective barrier materials. The testing procedure of the present invention makes use of the phenomena that surface tension lowering of the contacting aqueous phase facilitates the filling of small pores and the transport of fluid or particles in the fluid by wetting of the latex barrier.

SUMMARY OF THE INVENTION

Briefly stated, one aspect of the present invention relates to a method for the non-destructive testing of the integrity of a protective barrier material comprising applying an alternating electrical current across the protective barrier material for establishing a quality factor, Q, of the protective barrier material. The quality factor, Q, is measured at more than one frequency. The quality factor measurements so obtained are compared to a predetermined quality factor limit.

In another preferred embodiment, the present invention relates to a method for the non-destructive testing of the integrity of a protective barrier material comprising applying an alternating electrical current across the protective barrier material for establishing a conductivity, G, of the protective barrier material. The conductivity, G, is measured at more than one frequency. The conductivity measurements so obtained are compared to a predetermined conductivity limit.

In yet another preferred embodiment, the present invention relates to a method for the non-destructive testing of the integrity of a protective barrier material comprising releasably placing the protective barrier material on a conductive mandrel, the mandrel comprising circuitry for measuring electrical impedance. The mandrel is placed in an electrically conducting bath solution, the bath solution comprising an electrolyte and a wetting agent. An alternating current is applied to the bath solution and the conductivity and/or the quality factor are measured.

In still another preferred embodiment, the present invention relates to a method for the non-destructive testing of the integrity of a protective barrier material wherein the protective barrier material is formed directly on a mold which also serves as a mandrel. The protective barrier material is formed by dipping the mold-mandrel into a latex bath, removing the latex-covered mold-mandrel from the latex bath, and curing the latex on the mold-mandrel to provide the protective barrier material on the mold-mandrel. The mold-mandrel and the protective barrier material is then cooled to about room temperature prior to testing the integrity of the protective barrier material.

In an alternate embodiment, the present invention relates to an apparatus for the non-destructive testing of the integrity of a protective barrier material comprising a means for applying an alternating electrical current across the protective barrier material for establishing a quality factor, Q, of the protective barrier material. Means are provided for measuring the quality factor at more than one frequency. The quality factor measurements so obtained are compared to a predetermined quality factor limit.

In another alternate embodiment, the present invention relates to an apparatus for applying an alternating electrical current across the protective barrier material for establishing a conductivity, G, of the protective barrier material. Means are provided for measuring the conductivity at more than one frequency. The conductivity measurements so obtained are compared to a predetermined conductivity limit.

In yet another alternate embodiment, the present invention relates to an apparatus for the non-destructive testing of the integrity of a protective barrier material comprising releasably placing the protective barrier material on a conductive mandrel, the mandrel comprising circuitry for measuring electrical impedance. The mandrel is placed in an electrically conducting bath solution, the bath solution comprising an electrolyte and a wetting agent. An alternating current is applied to the bath solution and the conductivity and/or the quality factor are measured.

In still another alternate embodiment, the present invention relates to an apparatus comprising means for forming the protective barrier material on a mold-mandrel.

BRIEF DESCRIPTION OF THE DRAWING

For the purpose of illustrating the invention, there is shown in the drawing forms which are presently preferred; it being understood, however, that this invention is not limited to the precise arrangements and instrumentalities shown. In the drawing:

FIG. 1 is a partial cross-sectional view of a mandrel for testing a barrier material in accordance with one embodiment of the present invention;

FIG. 2 is a cross-sectional view of a mandrel in an electrically conducting bath solution in accordance with one embodiment of the present invention;

FIG. 3 is a schematic representation of an impedance analyzer as employed in accordance with the present invention; and FIG. 4 is a partial cross-sectional view of a mandrel in accordance with an alternate embodiment of the present invention.

DETAILED DESCRIPTION OF THE PREFERRED EMBODIMENTS

Preferably, the protective barrier with which the present invention is employed comprises a glove or a condom, but the invention could be employed with other types of dielectric or lossy dielectric barriers. The protective barrier material preferably comprises a synthetic polymeric material, for example, a polyurethane. Alternatively, the protective barrier material comprises a natural polymeric material, for example, rubber latex and modified latex. In addition, the protective barrier material may comprise a combination of a synthetic polymeric material and a natural polymeric material.

The outer surface of the protective barrier material may comprise or be at least partially coated with an additional material, for example, a lubricant. A suitable lubricant in accordance with the present invention includes a liquid lubricant, for example, silicon oil food grade, water-based propylene glycol or a gel, or a solid lubricant, such as a powder.

In accordance with the present invention, an alternating electrical current is applied across the protective barrier material for establishing a quality factor, Q, of the protective barrier material, and a conductivity, G, of the protective barrier material.

Q represents the ratio of energy stored to energy dissipated in an electrical circuit. Q also represents the ratio of the reactive part of the circuit impedance to the resistive part of the circuit impedance. Accordingly, as Q increases to a high quality factor, there is a reduced resistivity of the circuit impedance. In addition, the quality factor for barrier materials, particularly latex barriers without holes is considerably greater in magnitude than the quality factor for such barriers having micron-sized holes.

Preferably, the quality factor is measured at more than one frequency and the quality factor measurements are compared to a predetermined quality factor limit. This predetermined quality factor limit comprises a quality factor value below which the integrity of the protective barrier material is low and above which or about equal to the integrity of the protective barrier material is high.

The change in quality factor, or ΔQ, may be obtained from the quality factor measured at more than one frequency by taking the difference of the quality factors, for example, $Q_1 - Q_2$, where $Q_1$ is the quality factor obtained at one given frequency and $Q_2$ is the quality factor obtained at another given frequency. The ΔQ for a protective barrier material having a pinhole and the ΔQ of a protective barrier material which is free from pinholes may then be measured. The ratio of the ΔQ's may also be used as indication of the integrity of the protective barrier material.

Similarly, the change in conductivity, or ΔG, may be obtained from the conductivity measured at more than one frequency by taking the difference of the conductivities, for example, $G_1 - G_2$, where $G_1$ is the conductivity obtained at one given frequency and $G_2$ is the conductivity obtained at another given frequency. The ΔG for a protective barrier material having a pinhole and the ΔG of a protective barrier material which is free from pinholes may then be measured. The ratio of the ΔG's may also be used as an indication of the integrity of the protective barrier material.

In addition, the magnitude of conductivity, G, as well as the change in conductivity with frequency, ΔG, may be compared to a predetermined conductivity limit or change in conductivity limit. This predetermined conductivity limit or change in conductivity limit may comprise a value above which the integrity of the protective barrier material is unacceptable and below which the integrity of the carrier is acceptable.

With hole sizes having a radius of less than about 5 microns, Q obtained at low frequencies (10 to 500 Hertz) is low in value, increasing to much higher values as the frequency increases to above about 500 Hertz. The smaller the hole, the lower the frequency at which Q increase in value. Thus, Q, ΔQ, G and/or ΔG can be used as an indication of the hole size.

The correlation of the quality factor and conductivity measurements can be used as a check to further insure the integrity of the barrier membrane.

For example, the ΔQ's obtained by taking the difference between the quality factors at two different frequencies of a protective barrier material having a pinhole and a protective barrier material free from pinholes may be compared for a measurement independent of an absolute magnitude of the Q. The Q measurement is used rather than the a.c. impedance magnitude since the Q measurement has an increased sensitivity to the leakage resistance, especially for pinhole sizes in the range of about a few microns to less than one micron.

An impedance magnitude measurement for a pinhole consisting of a resistance in parallel with the membrane capacitance of the protective barrier material illustrates the decrease in sensitivity of this measurement to pinholes according to the following equation:

$$|Z| = \frac{R}{[1 + (RCw)^2]^{0.5}} = [G^2 + (wC)^2]^{-0.5}$$

where Z is impedance, R is the resistance through a pinhole (ohms), C is capacitance of the membrane (farads) and w is angular frequency (radians per seconds).

At low frequencies and small pinholes in protective barrier materials made of latex, the reactive contribution, wC, predominates over the conductive contribution, G. Despite the conductive contribution increasing more rapidly than the reactive contribution as the frequency increases for a micron-sized pinhole in a latex condom, the magnitude of the impedance even at frequencies greater than 1 kiloHertz is still reactive. Latex, unlike other polymer barrier/dielectric materials, generally exhibits a frequency dependent conductivity. Thus, the magnitude of the impedance is relatively insensitive to changes in G or the presence or absence of pinholes. Wetting agents decrease the interfacial impedance, such as the impedance due to electrode polarization. According to the present invention, a combination of wetting agents is used, greatly reducing Q. However, the reactive part of the impedance magnitude still dominates.

The integrity of the protective barrier material to potential tearing and/or bursting can be estimated due to the changes in the macromolecular structure of the barrier protective material under stress, which is reflected in a change of the dielectric constant. In addition, under stretching, minute pinholes may appear. The change in dielectric constant and resistance if small pinholes are present changes the Q and G measured at different frequencies. Thus, the increase in ΔQ and/or ΔG in a protective barrier material membrane which is free from pinholes would indicate a weak membrane prone to tearing or bursting. Although this would be a difficult measurement to make non-destructively on each protective barrier material, for example, on each condom or glove, it could be used quite effectively to evaluate samples of the integrity of batches of protective barrier materials.

In accordance with another embodiment of the present invention, the method for the non-destructive testing of the integrity of the protective barrier material comprises releasably placing the protective barrier material on a conductive mandrel. A preferred embodiment of a mandrel 10 for testing condoms in accordance with the present invention is depicted in FIG. 1. An alternate preferred embodiment of a mandrel 12 for testing gloves is depicted in FIG. 4. Furthermore, the mandrels 10 and/or 12 may comprise electronic circuitry shown functionally as 13 for measuring electrical impedance, Q, $\Delta Q$, G and/or $\Delta G$.

The mandrels 10 and/or 12 may be any suitable size for testing the integrity of the protective barrier material. In addition, the mandrels 10 and/or 12 are made of a suitable conductive material, for example, stainless steel, gold, conductive glass or conductive ceramic. The mandrels 10 and/or 12 may also be coated with a conductive film, for example, a gold film 14.

In the preferred embodiment of FIG. 1, the mandrel 10 comprises glass 16. An example of a suitable glass is PYREX®. In the alternate preferred embodiment of FIG. 4, the mandrel 12 comprises ceramic 18, coated with a gold film 14'. As indicated, the mandrels 10 and/or 12 may comprise electronic circuitry 13 for measuring electrical impedance, Q, $\Delta Q$, G and/or $\Delta G$. The electronic circuitry 13 may comprise analog, digital, discrete, thick film integrated circuitry or thin film integrated circuitry or combinations thereof. As set forth in FIG. 1, the mandrel 10 is generally hollow, so that a conductance coil 20 mounted on a conductance coil support rod 22 may be placed inside the mandrel 10. The electrical signals from the electronic circuitry 13 may be recorded and evaluated in several ways. For example, a high frequency modulated oscillator may be coupled to an antenna for transmission to a receiving antenna which in turn is coupled to a computer for recording and processing the information. The antenna on the mandrels 10 and/or 12 may have a specific directivity with the receiving antenna being variable in directivity so as to be synchronized to sequentially read a given mandrel from a group of mandrels. Thus, various types of antenna, such as antenna loops, may be positioned on top of the mandrel to transmit signals, as in a telemetering system generally known to those skilled in the art, to a central station. Standard techniques, for example, hard-wiring the electronic circuitry 13 via wires 24 and/or 24' on the mandrels 10 and/or 12 to a central station, for example, an impedance analyzer 26, via impedance analyzer wire 27 as depicted in FIG. 3, can also be used for transmitting electrical signals from the mandrel to a central station. A less complicated technique comprises placing a flashing red light on a mandrel to indicate a protective barrier material having a hole and/or a weakened protective barrier material.

To increase the sensitivity of a Q or G measurement, it is desirable to conduct the testing of the protective barrier material on the mandrels 10 and/or 12 at a resonance frequency.

In accordance with FIG. 2, after releasably placing a protective barrier material 28 on a conductive mandrel 10', the mandrel 10' may then be placed in an electrically conducting bath solution 30. The bath solution 30, housed within bath solution receptacle 32, preferably comprises an electrolyte and a wetting agent.

The electrolyte in the conducting bath solution 30 enhances the conductivity of the bath solution 30. An example of a suitable electrolyte to be used in the bath solution 30 in accordance with the present invention is sodium chloride (NaCl), although other suitable electrolytes would be apparent to one skilled in the art based on the present disclosure. In accordance with the present invention, the electrolyte is present in the conducting bath solution 30 preferably at a physiological concentration such as about 0.050 molar (M) to about 0.154M NaCl.

When a protective barrier material 28 having a hole or pore is placed into the bath solution 30, a portion of the electrically conducting solution 30 passes through the hole and wets the mandrel 10'. As a result, there is an increase in surface area on the mandrel 10' at the pore-mandrel interface, thereby decreasing the polarization impedance. Accordingly, a wetting agent is preferably used to decrease the quality factor for small holes, thereby increasing the measurement sensitivity. In accordance with the present invention, a suitable wetting agent to be used in the bath solution 30 comprises a surfactant and/or an alcohol. The surfactant may be non-ionic, anionic or cationic. An example of a suitable anionic surfactant is sodium dodecyl sulfate. An example of a suitable cationic surfactant is triammonium dodecyl bromide. An example of a suitable non-ionic surfactant is polyvinyl pyrrolidone (PVP). Preferably, the surfactant is PVP. In accordance with the present invention, the molecular weight range of the PVP is preferably about 40,000 to about 360,000, and more preferably, about 40,000. Other suitable non-ionic, anionic and cationic surfactants which may be used in accordance with the present invention will be apparent to one skilled in the art.

As indicated, the wetting agent may also comprise an alcohol. When the alcohol is used in conjunction with another wetting agent, for example, a surfactant, the alcohol increases the solubility and the wettability of the surfactant wetting agent. In accordance with the present invention, a suitable alcohol to be used in the electrolyte bath solution 30 is an alcohol miscible with the bath solution 30. Preferably, the alcohol includes isopropanol and ethanol. More preferably, the alcohol is ethanol. Other suitable alcohols to be used in the present invention would be apparent to one of ordinary skill in the art based on the present disclosure.

In accordance with the present invention, the wetting agent PVP is present in the bath solution at a concentration of about 0.5 grams/liter with 5% ethanol.

Further to the method for the non-destructive testing of the integrity of the protective barrier material 28, an alternating current is applied to the bath solution 30 and the conductivity, G, and the quality factor, Q, is measured. The alternating current source may be from an electrode which is placed into the bath solution 30. A suitable voltage to be applied to the bath solution 30 is about 0.050 to about 1 volt (V) and preferably, about 0.100 V. The electronic circuitry 13' on the mandrel 10' may be hard-wired via wire 24" to a central station, for example, the impedance analyzer 26.

In an alternate embodiment of the present invention, the protective barrier material may be formed directly on a mold-mandrel used to measure the conductivity and the quality factor of the protective barrier material.

"Mold-mandrel" refers to a mandrel on which the protective barrier material is first formed and then tested for its integrity. For example, the mold-mandrel may be dipped into a bath containing a suitable liquid polymeric material, for example, latex. The latex-covered mold-mandrel is removed from the latex bath. The latex on the mold-mandrel is then cured by heating the latex-covered mold-mandrel in suitable heating equipment, for example, an oven. This curing stage vulcanizes the protective latex barrier material on the mold-mandrel. The protective barrier material and the mold-mandrel are then cooled to about room temperature prior to testing the integrity of the protective barrier material on the mold-mandrel in the same manner as described hereinbefore for the testing of the integrity of the protective barrier material on a mandrel.

In accordance with another embodiment of the present invention, surgical latex gloves may be monitored for their integrity before and during surgery. Sweating in gloves produces a conductive interface so that the hand of the user can act as a testing mandrel. If there is no conductive material, a conductive dip on the hands may be used to insure a conductive interface. For example, a metallic coated plastic could be used on the palm of the hand of the user inside the glove. In addition, a very thin metallic coated plastic glove could be worn inside the latex glove.

Prior to surgery, the surgeon could dip a gloved hand in a sterilized conductive medium. The measured quality factor would indicate if the glove is permeable and/or has defects or holes. If a defect should develop during surgery and the surgeon's gloved hand is in a conductive medium, for example, blood, an indicator could set off a warning. The surgeon could also periodically check the integrity of a gloved hand by placing the gloved hand in a sterilized conductive medium and retesting.

In accordance with another embodiment of the present invention, thick film technology and thin film technology could be used to design a lightweight unobtrusive self-contained device for measuring the integrity of a protective barrier material for use by a surgeon. By being battery operated with rechargeable power sources, it would free the surgeon from obtrusive wires.

The present invention also relates to the sensing of defects or holes in other medical devices and medical packaging. For example, an implantable coated device, for example, a pacemaker, which is placed in the body in a conductive medium, could be tested by using an instrument for measuring the integrity of the pacemaker by placing the device in a tank of conductive medium.

The present invention will now be described in more detail with reference to the following specific, non-limiting examples.

EXAMPLE 1

In the following Example, 0.0154 molar (M) NaCl electrolyte solution and a 0.077M NaCl electrolyte solution were used.

Several holes in the micron range were made in American Trojan and German Fromms condoms. The holes were viewed under a microscope to locate them and quantitate their size. The integrity of the condoms were then measured in bath solutions with and without a wetting agent. The measured data indicates that with PVP, there was a marked lowering of the quality factor of condoms having holes compared to condoms without defects. When the ASTM test was carried out, wherein the condom was filled with 300 mL of water and suspended vertically, no visual drops of water on the outer surface of the condom were observed. When the FDA test was performed, wherein the condom was filled with 300 mL of water, the open end was closed off and the condom was rolled horizontally on an absorbent towel, no wet spots on the absorbent towel were observed. However, upon squeezing at the location where the hole was known to exist, the inner solution oozed out as a minute drop. Returning the condom to the mandrel produced reproducibly low quality factors in a PVP-electrolyte solution.

EXAMPLE 2

Various hole sizes were made in condoms, including $40\mu$, $16\mu$ and $2-3\mu$-sized holes according to microscopic measurements. Under the hydraulic tests, the $2-3\mu$ hole size did not demonstrate a hole defect. It is believed that the $2-3\mu$-sized hole is partially closed so that the diameter is below a micron, since even under an extreme hand pressure, only an extremely tiny dribble of fluid seeped out of the hole. The Q as measured was approximately four times smaller than with no hole. However, the Q was still relatively large compared to larger hole Q values. This could cause confusion with a very leaky membrane which does not have a noticeable hole defect and yet has Q values approaching the values for a condom having a $2-3\mu$ hole. Thus, another wetting agent, for example, ethyl alcohol in conjunction with PVP, is used to enhance the solution-condom interface wetting. The solution is drawn into the hole by capillary action to wet the condom-mandrel interface. This greatly increases the conductivity through the hole to markedly decrease the Q value for better detection of the hole sizes below a 1-micron diameter.

EXAMPLE 3

Holes less than 1 micron in size were made in a condom. Five percent ethyl alcohol was added to a testing tank containing the 0.077M NaCl solution and 0.5 g/L of PVP. The combination of the PVP and ethyl alcohol in this solution enhanced the wetting so that holes less than a micron in diameter were readily detectable with low quality factors. The ASTM and FDA hydraulic leak tests indicated no holes in the membrane. Even squeezing the membrane around the sub-micron-sized hole produced no leakage of water at the hole site. The a.c. Q measurement and conductivity demonstrated with microscopic viewing and pictures that two holes of less than 1 micron in diameter were present in the membrane.

These examples demonstrate that a two-state device can be designed to determine the existence or nonexistence of holes in protective barriers, for example, gloves and condoms. The Q measurements have far greater sensitivity than the alternating current impedance magnitude to detect holes and defects, especially for hole sizes in the few micron range or less than 1 micron. The conductance can also be used to detect holes and defects.

The present invention may be embodied in other specific forms without departing from the spirit or essential attributes thereof and, accordingly, reference should be made to the appended claims, rather than to the foregoing specification as indicating the scope of the invention.

We claim:

1. A method for the non-destructive testing of the integrity of a protective barrier material comprising
   (a) applying an alternating electrical current across the protective barrier material for establishing a quality factor, Q, of the protective barrier material;
   (b) measuring the quality factor, Q, at more than one frequency; and
   (c) comparing the quality factor measurements obtained to a predetermined quality factor limit.

2. The method of claim 1 wherein quality factor measurements below the quality factor limit indicate that the integrity of the barrier material is low and quality factor measurements at or above the quality factor limit indicate the integrity of the barrier material is high.

3. The method of claim 1 comprising
   (a) placing the protective barrier material on a conductive mandrel, the mandrel comprising circuitry for measuring electrical impedance and the quality factor;
   (b) placing the mandrel in an electrically conducting bath solution, the bath solution comprising an electrolyte and a wetting agent; and
   (c) applying an alternating current to the bath solution.

4. The method of claim 1 comprising placing the protective barrier material on a conductive mandrel, the mandrel comprising circuitry for measuring electrical impedance.

5. The method of claim 4 further comprising placing the mandrel in an electrically conducting bath solution, the bath solution comprising an electrolyte.

6. The method of claim 5 further comprising applying an alternating current to the bath solution.

7. The method of claim 4 further comprising placing the mandrel in an electrically conducting bath solution, the bath solution comprising a wetting agent.

8. The method of claim 7 further comprising applying an alternating current to the bath solution.

9. The method of claim 1 wherein the protective barrier material comprises a synthetic polymeric material or a natural polymeric material.

10. The method of claim 1 wherein the protective barrier material is at least partially coated with a lubricant.

11. The method of claim 3 wherein the electrolyte comprises sodium chloride.

12. The method of claim 3 wherein the wetting agent comprises a surfactant or an alcohol.

13. The method of claim 12 wherein the surfactant comprises polyvinyl pyrrolidone.

14. The method of claim 12 wherein the alcohol comprises an alcohol miscible with the bath solution.

15. The method of claim 14 wherein the alcohol comprises ethanol or isopropanol.

16. The method of claim 1 wherein the protective barrier comprises a glove or a condom.

17. The method of claim 1 wherein the protective barrier material is formed on a mold-mandrel, comprising (i) dipping the mold-mandrel into a latex bath; (ii) removing the latex-covered mold-mandrel from the latex bath; (iii) curing the latex on the mold-mandrel to provide the protective barrier material on the mold-mandrel; and (iv) cooling the mold-mandrel and the protective barrier material to about room temperature prior to testing the integrity of the protective barrier material.

18. An apparatus for the non-destructive testing of the integrity of a protective barrier material comprising
   (a) means for applying an alternating electrical current across the protective barrier material for establishing a quality factor, Q, of the protective barrier material; and
   (b) means for measuring the quality factor, Q, at more than one frequency, and for comparing the quality factor measurements obtained to a predetermined quality factor limit.

19. The apparatus of claim 18 wherein quality factor measurements below the quality factor limit indicate that the integrity of the barrier material is low and quality factor measurements at or above the quality factor limit indicate the integrity of the barrier material is high.

20. The apparatus of claim 18 comprising
   (a) a conductive mandrel on which the protective barrier material is placed, the mandrel comprising circuitry for measuring electrical impedance and the quality factor;
   (b) an electrically conducting bath solution in which the mandrel is placed, the bath solution comprising an electrolyte and a wetting agent; and
   (c) means for applying an alternating current to the bath solution.

21. The apparatus of claim 18 comprising a conductive mandrel on which the protective barrier material is placed, the mandrel comprising circuitry for measuring electrical impedance.

22. The apparatus of claim 21 further comprising an electrically conducting bath solution in which the mandrel is placed, the bath solution comprising an electrolyte.

23. The apparatus of claim 22 further comprising means for applying an alternating current to the bath solution.

24. The apparatus of claim 21 further comprising an electrically conducting bath solution in which the mandrel is placed, the bath solution comprising a wetting agent.

25. The apparatus of claim 24 further comprising means for applying an alternating current to the bath solution.

26. The apparatus of claim 18 wherein the barrier material comprises a synthetic polymeric material or a natural polymeric material.

27. The apparatus of claim 18 wherein the protective barrier material is at least partially coated with a lubricant.

28. The apparatus of claim 20 wherein the electrolyte comprises sodium chloride.

29. The apparatus of claim 20 wherein the wetting agent comprises a surfactant or an alcohol.

30. The apparatus of claim 29 wherein the surfactant comprises polyvinyl pyrrolidone.

31. The apparatus of claim 29 wherein the alcohol comprises an alcohol miscible with the bath solution.

32. The apparatus of claim 31 wherein the alcohol comprises ethanol or isopropanol.

33. The apparatus of claim 18 wherein the protective barrier comprises a glove or a condom.

34. The apparatus of claim 18 comprising a means for forming the protective barrier material on a mold-mandrel.

* * * * *